(12) United States Patent  
Horvath

(10) Patent No.: US 8,517,699 B2
(45) Date of Patent: Aug. 27, 2013

(54) CENTRIFUGAL PUMP WITH OFFSET VOLUTE

(75) Inventor: David Horvath, Euclid, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 468 days.

(21) Appl. No.: 12/336,283

(22) Filed: Dec. 16, 2008

(65) Prior Publication Data

US 2010/0150749 A1  Jun. 17, 2010

(51) Int. Cl.
*F04B 35/04* (2006.01)

(52) U.S. Cl.
USPC ............................... 417/410.1; 417/321

(58) Field of Classification Search
USPC ........................................ 417/410.1
See application file for complete search history.

(56) References Cited

U.S. PATENT DOCUMENTS

| | | | |
|---|---|---|---|
| 5,049,134 A * | 9/1991 | Golding et al. | 604/151 |
| 7,189,260 B2 | 3/2007 | Horvath et al. | |
| 7,699,586 B2 | 4/2010 | LaRose et al. | |
| 2004/0047753 A1 | 3/2004 | Horvath et al. | |
| 2006/0024182 A1* | 2/2006 | Akdis et al. | 417/423.12 |
| 2006/0122456 A1 | 6/2006 | LaRose et al. | |
| 2006/0245959 A1 | 11/2006 | LaRose et al. | |
| 2007/0078293 A1 | 4/2007 | Shambaugh, Jr. et al. | |
| 2007/0100196 A1 | 5/2007 | LaRose et al. | |
| 2007/0253842 A1 | 11/2007 | Horvath et al. | |
| 2010/0069847 A1 | 3/2010 | LaRose et al. | |

* cited by examiner

*Primary Examiner* — Anh Mai
*Assistant Examiner* — Andrew Coughlin
(74) *Attorney, Agent, or Firm* — Trego, Hines & Ladenheim, PLLC

(57) ABSTRACT

A pump includes: (a) an elongated pump housing having first and second ends; (b) a primary impeller mounted in the housing for rotation about an axis, the impeller comprising a plurality of vanes whose outer tips define an impeller plane; (c) an inlet disposed in fluid communication with the primary impeller; and (d) an annular volute housing communicating with the primary impeller and with an outlet, where the volute housing is axially offset from the impeller plane.

10 Claims, 3 Drawing Sheets

CENTRIFUGAL PUMP WITH OFFSET VOLUTE

BACKGROUND OF THE INVENTION

This invention relates generally to pumps, and more particularly to centrifugal pumps used in medical applications.

It is known to use centrifugal pumps as cardiac assist devices, also known as left or right ventricular assist devices ("LVAD" or "RVAD"). In such applications, the pump is implanted in the patient along with a power source and a control system. Alternatively, the power source and control system may be located externally.

A centrifugal pump includes a rotating impeller contained in a housing which defines an inlet, and an annular chamber which surrounds the impeller, which is commonly referred to as a "volute". Fluid flow enters the impeller near its center and exits from the periphery of the impeller. The flow exiting the impeller is collected in the volute and channeled to an outlet. Conventional centrifugal pump design places the volute section in axial alignment with the outside diameter of the impeller. This results in a very short fluid residence time in the impeller and volute, and a greater residence time of recirculating fluid in the more remote sections of the pump.

When used as a blood pump for a ventricular assist system, extended residence time of blood within a pump can cause thrombus (clot) formation, and hemolysis (damage of red blood cells), both of which are undesirable.

BRIEF SUMMARY OF THE INVENTION

These and other shortcomings of the prior art are addressed by the present invention, which provides a centrifugal pump that minimizes residence time of fluids therein.

According to one aspect of the invention, a pump includes: (a) an elongated pump housing having first and second ends; (b) a primary impeller mounted in the housing for rotation about an axis, the impeller comprising a plurality of vanes whose outer tips define an impeller plane; (c) an inlet disposed in fluid communication with the primary impeller; and (d) an annular volute housing communicating with the primary impeller and with an outlet, where the volute housing is axially offset from the impeller plane.

According to another aspect of the invention, a cardiac assist device includes: (a) an elongated housing having first and second ends; (b) a primary impeller mounted in the housing for rotation about an axis, the impeller defining an impeller plane; (c) an inlet disposed in fluid communication with the primary impeller; and (d) an annular volute housing communicating with the primary impeller and with an outlet, where the volute housing is axially spaced away the impeller plane. The housing, the primary impeller, the inlet, and the volute housing are constructed from biologically compatible materials.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
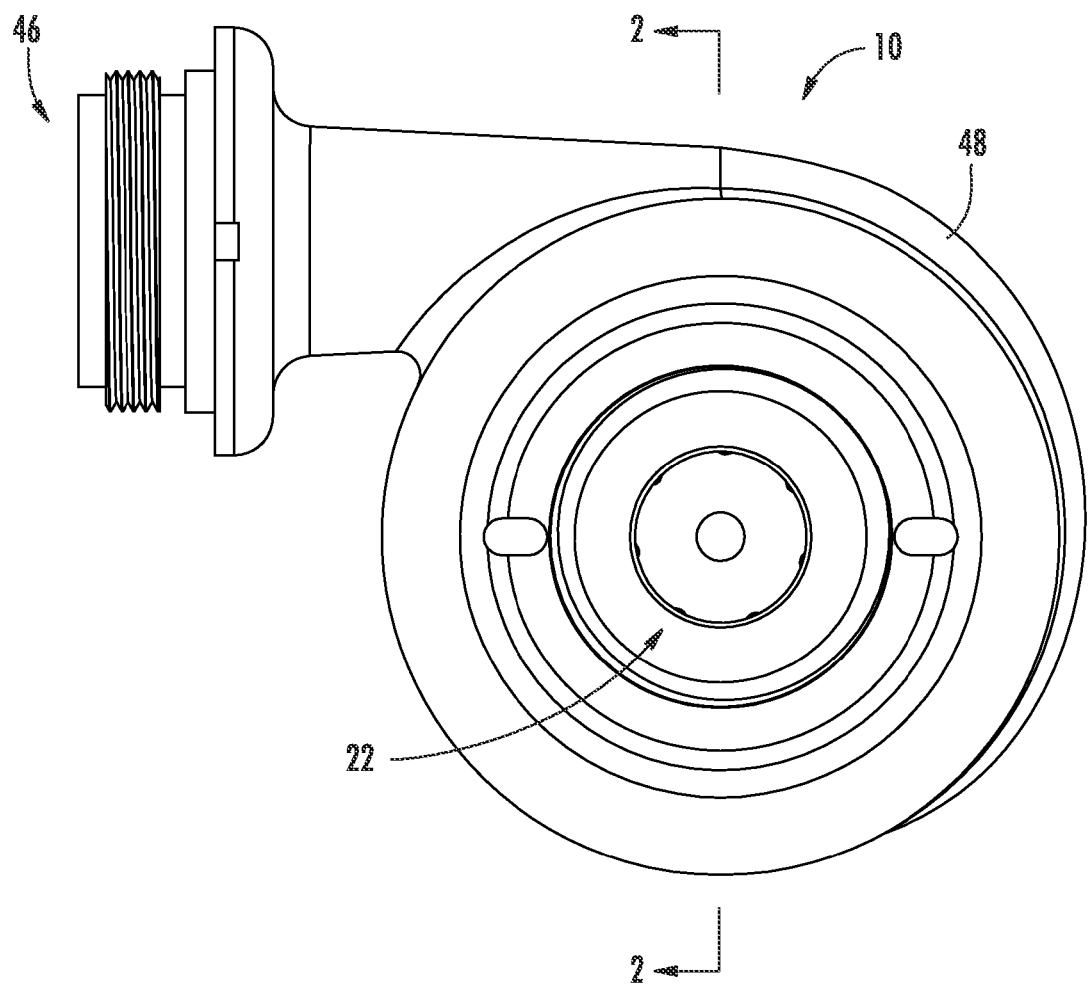
FIG. 1 is a side view of a centrifugal pump constructed according to an aspect of the present invention.
Figure 2:
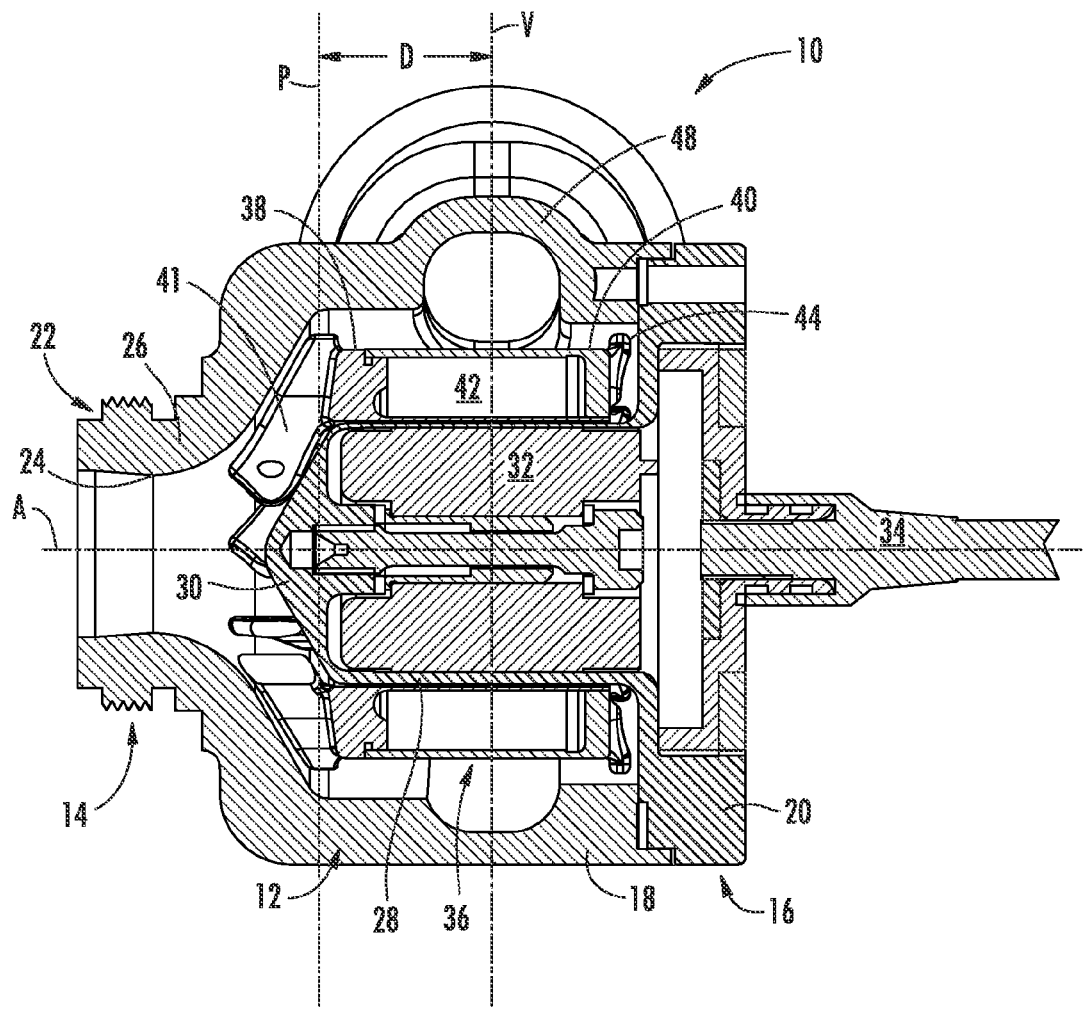
FIG. 2 is a cross-sectional view of the centrifugal pump of FIG. 1.

Referring to the drawings wherein identical reference numerals denote the same elements throughout the various views, FIGS. 1 and 2 depict a centrifugal pump 10 of the type used to pump blood or similar products. The pump 10 includes a pump housing 12 with opposed first and second ends 14 and 16, and a central axis "A".

In the illustrated example the pump housing 12 is split into a body 18 and a separate cover plate 20. The cover plate 20 closes off the second end 16 and may be secured to the body 18 by one or more fasteners, for example.

A central portion of the pump housing 12 is generally cylindrical. The first end 14 of the pump housing 12 defines a centrally-located, axially-aligned inlet 22 of a conventional profile with a throat 24 and a generally conical portion 26.

A stator housing 28, which may be integral with the cover plate 20, extends from the cover plate 20 into the center of the pump housing 12. The distal end of the stator housing 28 terminates in a conical surface 30. An electrical stator 32 comprising a plurality of coil windings is contained in the interior of the stator housing 28. A cable 34 which penetrates the cover plate 20 provides electrical connections for power, control, and sensing functions to the stator 32.

A rotor 36 is disposed in the pump housing 12, surrounding the stator housing 28. The rotor 36 is generally cylindrical with first and second ends 38 and 40 corresponding to the first and second ends 14 and 16 of the pump housing 12. The rotor 36 includes a primary impeller 41 at its first end 38 which comprises an annular array of vanes located between the inlet 22 and the conical surface 30. The outer tips of the vanes of the primary impeller 41 lie generally within an impeller plane, which is shown schematically at "P" in FIG. 2. One or more permanent magnets 42 are disposed in an annular array within the walls of the rotor 36. A secondary impeller 44 comprising an annular array of vanes is located at the second end 40 of the rotor 36. The rotor 36 and the stator 32 operate as a brushless DC motor through the application of varying electrical currents to the stator 32 through the cable 34, in a known manner.

All of the portions of the pump 10 which will come into contact with blood or tissue, including the pump housing 12 and the rotor 36, are constructed from known biologically compatible materials such as titanium, medical grade polymers, and the like.

Together, the stator housing 28 and the rotor 36 are configured so as to operate as a hydrodynamic bearing for the rotor 36 in operation. Specifically, the secondary impeller 44 causes a small portion of the blood flowing through the primary impeller 41 to flow axially to the cover plate 20, radially inward through the secondary impeller 44, and axially towards the primary impeller 41 between the rotor 36 and the stator housing 28. This bearing and recirculation function is explained in more detail in U.S. Pat. No. 7,189,260 to Horvath, et al.

The pump housing 12 includes an annular passage which collects the flow exiting the primary impeller 41 and channels it to a single outlet 46 (see FIG. 1). This passage is referred to as a "volute" or volute housing 48. As shown in FIG. 2, the axial position of the volute housing 48 is substantially offset away from the plane P of the primary impeller 41 and towards the cover plate 20. The actual offset distance between the impeller plane P and the midplane "V" of the volute housing 48, denoted "D", is not a critical dimension, however generally the volute housing 48 is offset as much as possible towards the cover plate 20 within the physical constraints of the pump housing 12 and the walls of the volute housing 48.

In the illustrated example, the midplane V of the volute housing 48 is located approximately halfway between the impeller plane P and the second end 16 of the pump housing 12.

Figure 3:
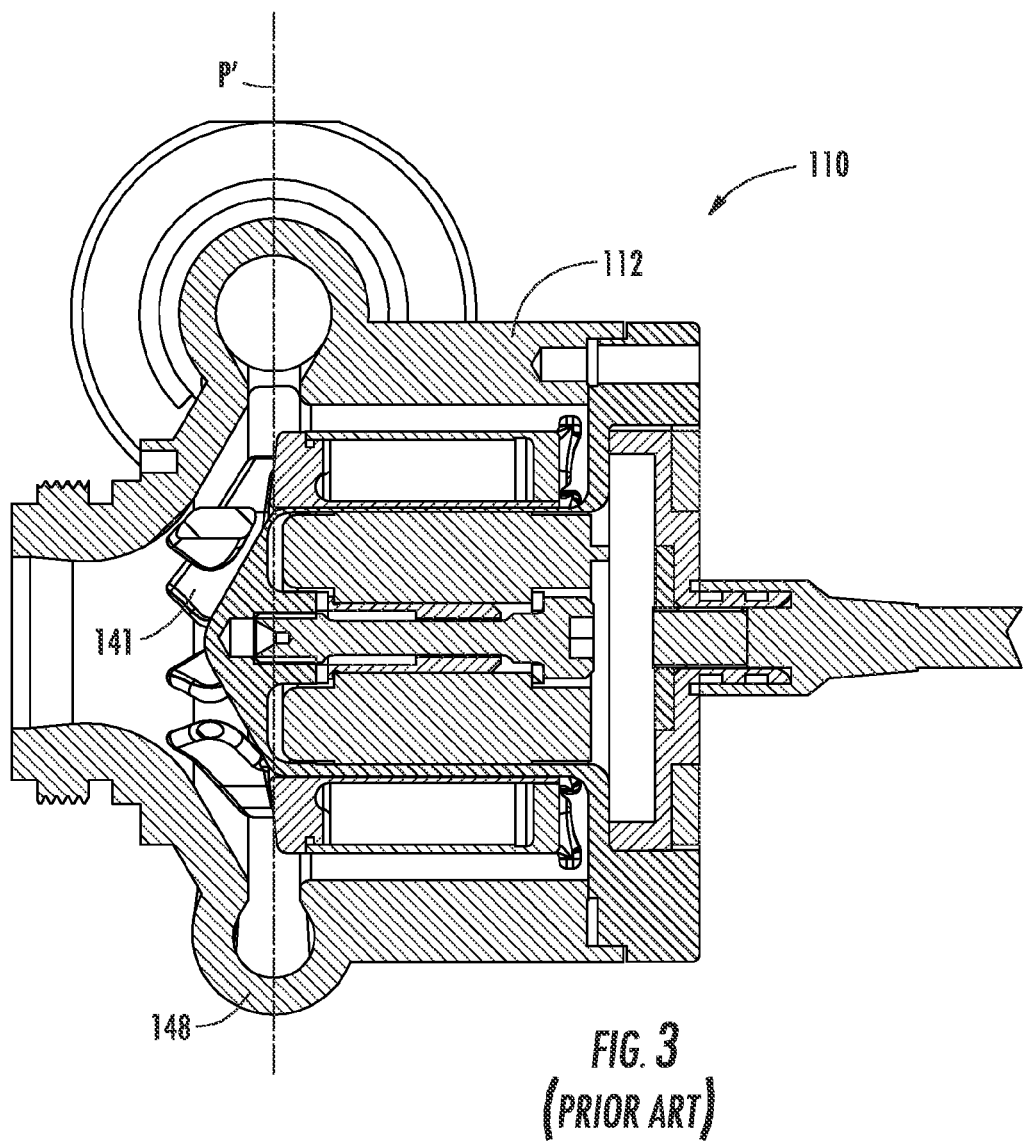
FIG. 3 is a cross-sectional view of a prior art centrifugal pump.

This positioning of the volute housing 48 is in substantial contrast to a conventional centrifugal pump design. For Example, FIG. 3 illustrates a prior art centrifugal pump 110 having a pump housing 112, a primary impeller 141, and a volute housing 148. It can be seen that the volute housing 148 and the outer vane tips of the primary impeller 141 line substantially in a single plane, denoted "P'".

Surprisingly, it has been found that the offset position of the volute housing 48 greatly decreases fluid residence time during operation of the pump 10. By "residence time" it is meant the duration that a specific, identifiable volume of fluid remains within the pump 10, from the time it enters the inlet 22 until it finally exits the outlet 46. Residence time is not necessarily related to the average mass or volume flow rate. For example, it has been found that the prior art pump 110 may exhibit a relatively long residence time. Flow visualization has revealed that peak residence time in the pump 10 is approximately cut in half as compared to the prior art pump 110.

Despite the unconventional placement, overall pump performance is maintained across its operating range. Mechanical efficiency of the pump 10 is also virtually unchanged by moving the volute housing 48.

The reduction in residence time is especially advantageous when using the pump 10 as an implantable blood pump for a ventricular assist system, e.g. an LVAD or RVAD, in which it is desired to minimize residence time of blood to avoid thrombus (clot) formation, and hemolysis (damage of red blood cells). However, the concepts described herein are also useful for other fluid pumping applications where the working fluid is sensitive to shear and mechanical damage, such as whole blood, plasma, serum, or other therapeutic fluids containing complex molecules.

The foregoing has described a centrifugal pump. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A pump, comprising:
   (a) an elongated pump housing having first and second ends;
   (b) a centrifugal primary impeller mounted in the housing for rotation about an axis, the primary impeller comprising a plurality of vanes whose outer tips define an impeller plane;
   (c) an inlet disposed in fluid communication with the primary impeller; and
   (d) a volute housing extending in a spiral shape around the pump housing, the volute housing communicating with the primary impeller and with an outlet, the volute housing extending radially beyond axially-adjacent portions of the pump housing relative to the axis, where the volute housing is axially offset from the impeller plane, such that the volute housing is separated from the primary impeller in the axial direction by a cylindrical portion of the pump housing;
   wherein the primary impeller is carried at one end of a generally cylindrical rotor and a secondary impeller is carried at a second end of the rotor.

2. The pump of claim 1, wherein the rotor is mounted around a stator housing disposed within the pump housing.

3. The pump of claim 2, wherein:
   (a) an electrical stator winding is disposed in the stator housing; and
   (b) the rotor includes at least one magnet disposed therein.

4. The pump of claim 2 wherein the stator housing includes a conical surface at one end thereof, and the primary impeller is disposed between the conical surface and the inlet.

5. The pump of claim 1, wherein the volute housing is located approximately halfway between the impeller plane and the second end of the pump housing.

6. A cardiac assist device, comprising:
   (a) an elongated housing having first and second ends;
   (b) a centrifugal primary impeller mounted in the housing for rotation about an axis, the primary impeller defining an impeller plane;
   (c) an inlet disposed in fluid communication with the primary impeller; and
   (d) a volute housing extending in a spiral shape around the pump housing, the volute housing communicating with the primary impeller and with an outlet, the volute housing extending radially beyond axially-adjacent portions of the pump housing, where the volute housing is axially spaced away from the impeller plane, such that the volute housing is separated from the primary impeller in the axial direction by a cylindrical portion of the pump housing;
   wherein the housing, the primary impeller, the inlet, and the volute housing are constructed from biologically compatible materials; and
   wherein the primary impeller is carried at one end of a generally cylindrical rotor and a secondary impeller is carried at a second end of the rotor.

7. The cardiac assist device of claim 6, wherein the rotor is mounted around a stator housing disposed within the pump housing.

8. The cardiac assist device of claim 7, wherein:
   (a) an electrical stator winding is disposed in the stator housing; and
   (b) the rotor includes at least one magnet disposed therein.

9. The cardiac assist device of claim 7, wherein the stator housing includes a conical surface at one end thereof, and the primary impeller is disposed between the conical surface and the inlet.

10. The cardiac assist device of claim 6, wherein the volute housing is located approximately halfway between the impeller plane and the first end of the pump housing.

* * * * *